US00PP12665P2

(12) United States Plant Patent
Duncan

(10) Patent No.: US PP12,665 P2
(45) Date of Patent: May 28, 2002

(54) SEASHORE PASPALUM PLANT 'SEA ISLE 1'

(75) Inventor: Ronny R. Duncan, Griffin, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/552,045

(22) Filed: Apr. 19, 2000

(51) Int. Cl.[7] ..... A01H 5/00
(52) U.S. Cl. ..... Plt./388

(58) Field of Search ..... Plt./388

*Primary Examiner*—Bruce R. Campell
*Assistant Examiner*—Annette H. Para
(74) *Attorney, Agent, or Firm*—Needle & Rosenberg, P.C.

(57) ABSTRACT

A vegetatively reproduced seashore paspalum cultivar, developed from a segregating seed collection of unknown parentage, is named 'Sea Isle 1'. It is distinguished by high tolerance to salinity, dark green color, fine textured leaves, and high turf quality and density. These distinguishing characteristics make it particularly suitable as a turfgrass for lawns and golf courses.

2 Drawing Sheets

SUMMARY OF THE INVENTION

The present invention comprises a new and distinct plant of *Paspalum vaginatum* O. Swartz which has been given the name 'Sea Isle 1'. The following traits have been repeatedly observed and are the most pronounced characteristics of this new cultivar when grown in Georgia, and in combination, they distinguish it from Adalayd®, the most closely related variety.

1. High tolerance to salinity
2. Dark green color
3. Fine textured leaves with high turf quality and density

BRIEF DESCRIPTION OF THE FIGURES

FIG. 1 shows the Sea Isle 1 plant growing in a turf setting, producing inflorescences (commonly referred to as spikes), which are highlighted against white paper on a clipboard.

FIG. 2 shows typical rhizomes of Sea Isle 1.

DETAILED DESCRIPTION

Background of the Invention

*Paspalum vaginatum* O. Swartz is a grass in the Panicoideae subfamily which inherently colonizes saline ecosystems, e.g. along sea coasts and on brackish sands. Commonly referred to as "seashore paspalum", it is an ecologically aggressive, littoral warm-season perennial grass. species. It is both rhizomatous and stoloniferous. Because it can tolerate waterlogged conditions and periodic, meso-saline flooding, it has been useful for erosion control on salinity-sensitive lands and areas subjected to tidal influences, e.g. for beach preservation. The grass occurs in the wild in both hemispheres. In the Americas, it is found naturally almost exclusively along the Atlantic coastline in marshy, brackish ecosystems. In Australia, it is found in tropical heaths, tropical and subtropical rainforests, semi-arid shrub woodlands, acacia shrublands, and mangrove swamps.

Generally, *P. vaginatum* is a self-incompatible, diploid species. The diploid chromosome number recognized for the species is 20, and the genome of this species is the "D" genome. It has a $C_4$ method of carbon fixation, using the NADP-ME pathway, which if characteristic for grasses that occur in moist ecosystems.

*P. vaginatum* has been introduced into salt-affected areas as the need for forages, land reclamation and turf have increased. The variety Adalayd® has been widely used in Australia as a lawngrass, although its use on bowling greens was curtailed when superdwarf bermuda grasses were introduced to the country. *P. vaginatum* was identified on a marsh golf course at the Sea Island Golf Club of Georgia, in the southeastern United States, where the grass was already established along the golf course fairwways when the course was built in 1925. *P. vaginatum* was introduced sporadically throughout the 1970s and 1980s for golf course and home lawn use, and one variety from Australia became reasonably well-known in the United States, Adalayd® (U.S. Plant Pat. No. 3,939). However, this variety was not managed effectively in the United States, and the lack of optimization of fertilization regimes and irrigation requirements led to disenchantment about its performance. With the introduction of the dwarf bermudagrasses and other warm season grasses, the use of a seashore paspalum variety as a turfgrass has been minimal. In the late 1980s a variety of seashore paspalum was introduced to a golf course in Honolulu, Hi., from Sea Island, Ga., and is now referred to as 'Salam' (an unpatented variety).

With increasing pressures on golf course developers to use coastal venues and reclaimed water sources (or brackish water), there is a need for a high-quality seashore paspalum turfgrass adapted to the United States.

ORIGIN OF THE INVENTION

Sea Isle 1 is a selection from a segregating seed collection of unknown parentage from Argentina. Sea Isle 1 was selected on the basis of its aggressive growth habit and tolerance to close mowing, important attributes for turf user.

PROPAGATION

Sea Isle 1 can be propagated asexually through sprigs or sod. Sprigging rates can vary from a minimum of 5 bushels per 1000 $ft^2$ (200 bushels/acre) to normal warm-season grass rates of 400–6000 bushels per acre. To establish purity and minimize cross-contamination in plots, single stolons of Sea Isle 1 were initially planted in soilless media, then continuously increased in the greenhouse until ready for field planting on golf courses or sports fields. Foundation fields are planted from this greenhouse-grown material. Asexual reproduction demonstrates that the unique features of 'Sea Isle 1' are stable and are reproduced true-to-type in subsequent generations. Sea Isle 1 was asexually propagated at the Georgia Agricultural Experiment Station, College of Agricultural and Environmental Sciences, Department of Soil and Crop Sciences, Griffin, Ga., U.S.A.

Sea Isle 1 can also be propagated through in vitro tissue culturing (for general protocols, see C.A. Cardono and R.R. Duncan 1997 Crop Science 37:1297–1302). The best explants for induction of embryogenic callus are immature inflorescences.

Botanical description:

*Culms.*—The flowering culms are erect or basally decumbent, ranging in height from 8–15 cm (unmowed) with 5–8 glabrous nodes.

*Leaves.*—Mid-culm leaves are fine-textured, do not have sheath or blade auricles, and are distichous. The blades are 50 mm long, approximately 2 mm wide, linear and glabrous, tapering to a narrow apex. The prophyllum is 20 mm long. The 1 mm ligule is membraneous and truncate with a pubescent collar. The leaf edges are smooth and the leaf veins are obscure.

*Stolons.*—Nodes are pubescent, and the internode length is 7–9 mm.

*Inflorescence.*—The inflorescence is composed of two primary racemes, 20–25 mm in length, with 16–25 twin-rowed spikelets on each primary raceme, and is fully exserted at maturity. Each spikelet is solitary, plano-convex, subsessile, elliptic, 2.5 mm long, and 0.9–1.5 mm wide. Anthers are 1.2–1.4 mm long. The glumes are glaborous.

*Seed.*—Rarely produced, but are typically 2.5 mm long and 1.5 mm wide, narrowly obovate, subacute, and slightly concavo-convex. The seed is straw-colored when mature.

*Salt tolerance and growth rates.*—Sea Isle 1 was compared to the variety Adalayd® in a standard laboratory salinity stress study. As shown in Table 1, Sea Isle 1 was consistently more tolerant of salt, both in terms of its growth at a relatively high salt concentration (40 deciSiemens per meter, or $dSm^{-}1$) as well as in the amount of salinity required (EC) to result in a 25% reduction in growth (for comparison, ocean water has a conductivity of 54 $dSm^{-}1$). In addition, Sea Isle 1 is more aggressive in its overall growth rate in the absence of salt.

TABLE 1

| | Growth (g/container[a]) | | | | EC @ growth reduction | |
|---|---|---|---|---|---|---|
| | No Salt | | 40 $dSm^{-}$ | | $dSm^{-}$ | |
| | Shoot | Root | Shoot | Root | Shoot | Root |
| Adalayd ® | 0.23 | 0.20 | 0.08 | 0.13 | 7.64 | 15.79 |
| SEA ISLE 1 | 0.70* | 0.42* | 0.22* | 0.32* | 16.58 | 16.98 |
| F test | *** | *** | *** | *** | 0.38 | 0.38 |
| | Crown | Total | Crown | Total | | |
| Adalayd ® | 0.57 | 1.00 | 0.37 | 0.59 | | |
| SEA ISLE 1 | 0.80 | 1.92* | 0.63# | 1.17* | | |
| F test | *** | *** | *** | *** | | |

*, , *, # 0.001, 0.01, 0.05, and 0.1 probability levels, respectively (Dunnett T Test; Steele and Torrie, 1960, Principles and Procedures of Statistics, McGraw-Hill, New York)
[a]5 cm top diameter × 20 cm depth = container

*Leaf color.*—The color of turfgrasses can vary significantly depending on environmental conditions. When compared side-by-side, the following Royal Horticultural Society color chart values are obtained for Sea Isle 1 and Adalayd®: Sea Isle 1: 137B. Adalayd®: 138A.

*Turf quality.*—Sea Isle 1 is a fine-textured cultivar (smaller leaves and shorter internodes) when compared to Adalayd®, which is an intermediate-textured cultivar. When mowed at the same height, Sea Isle 1 has a more dense canopy than Adalayd®. Overall turf quality ratings, on a scale of 1.0 to 9.0, where 9.0 is the best, are 8.0 for Sea Isle 1 and 5.0 for Adalayd®. The overall turf quality rating is a visual rating based on cosmetic appearance, color, leaf texture, denseness of canopy and uniformity of stand.

*Disease resistance.*—Sea Isle 1 has good resistance to dollar spot, and moderate laboratory resistance to mole crickets. Field mole cricket evaluations reveal that there is no significant loss in turf shoot quality with heavy infestations.

What is claimed:

1. A new and distinct plant of *Paspalum vaginatum* as herein shown and described, that is characterized by a unique combination of high tolerance to salinity, dark green color, and high turf quality and density.

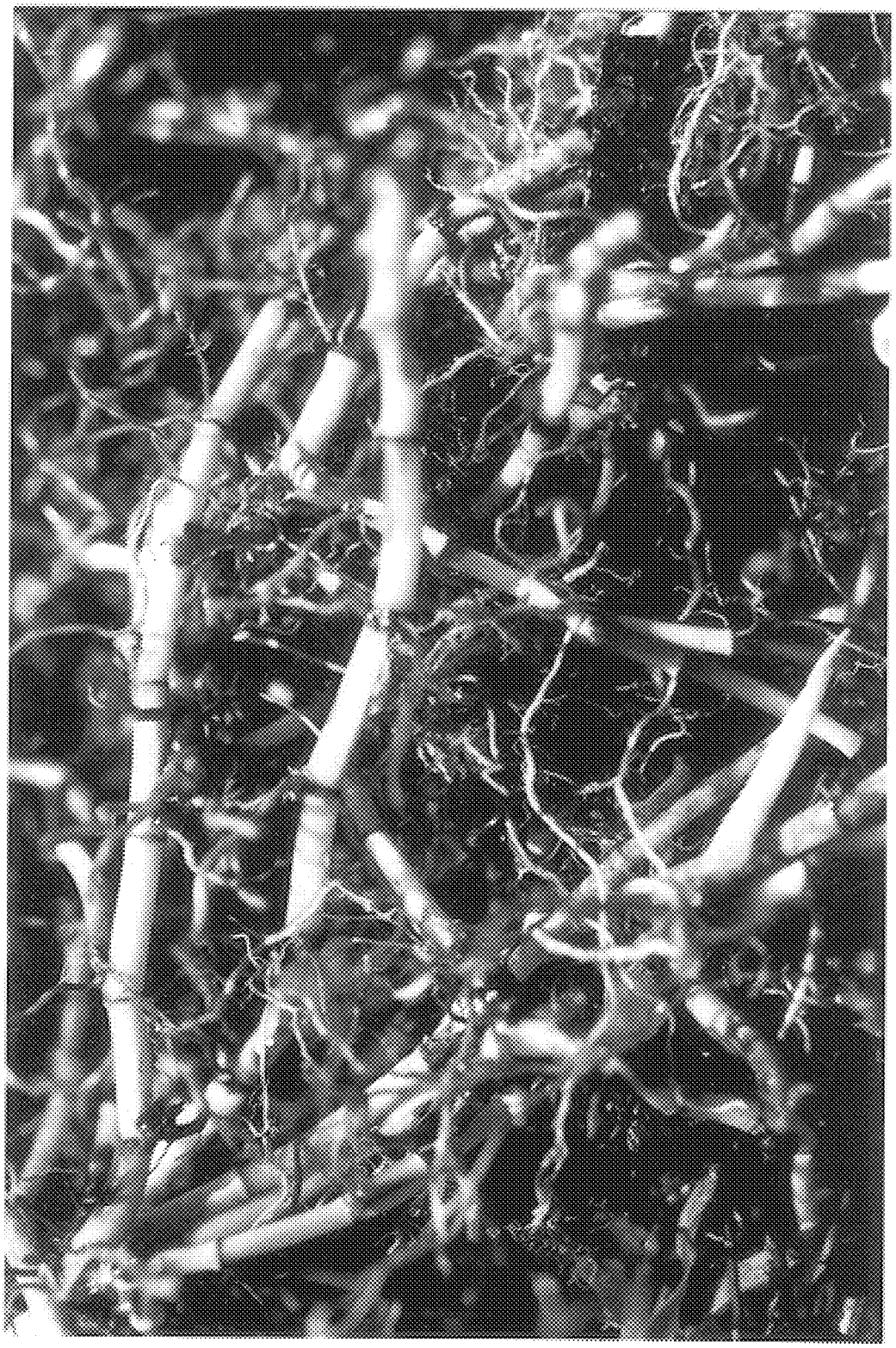

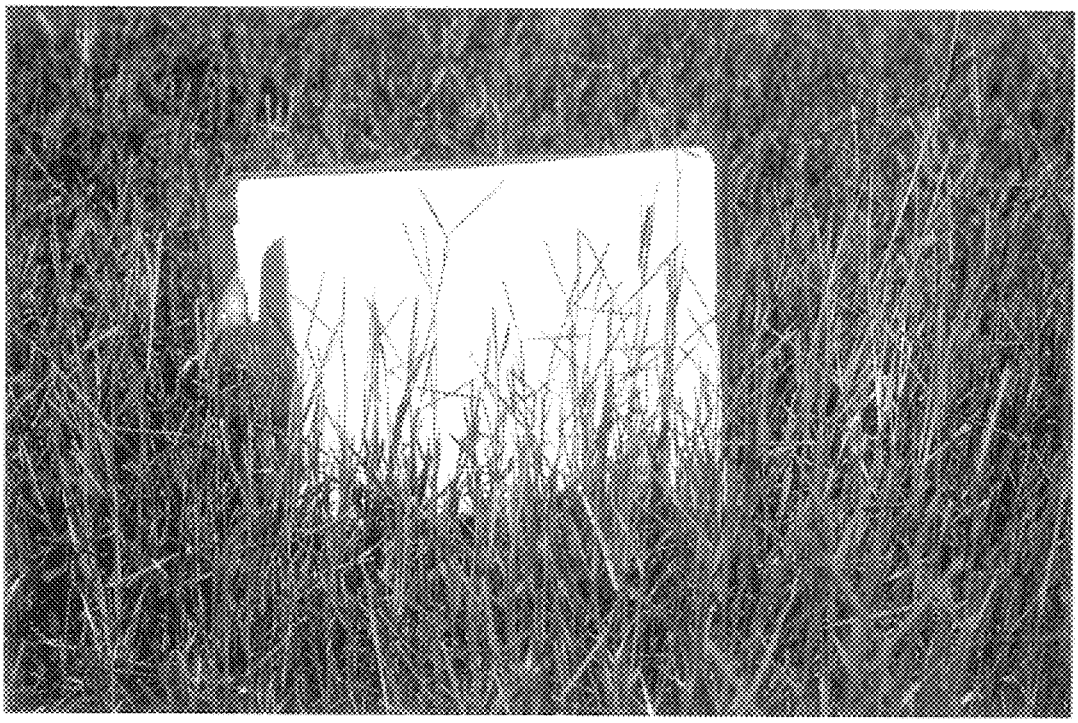

* * * * *